United States Patent
Kouznetsov

(10) Patent No.: US 6,255,653 B1
(45) Date of Patent: Jul. 3, 2001

(54) DIFFUSION-TYPE NDIR GAS ANALYZER WITH IMPROVED RESPONSE TIME DUE TO CONVECTION FLOW

(75) Inventor: Andrian Kouznetsov, Santa Barbara, CA (US)

(73) Assignee: Engelhard Sensor Technologies, Inc., Iselin, NJ (US)

( * ) Notice: Subject to any disclaimer, the term of this patent is extended or adjusted under 35 U.S.C. 154(b) by 0 days.

(21) Appl. No.: 09/695,267

(22) Filed: Oct. 24, 2000

Related U.S. Application Data

(63) Continuation of application No. 08/958,160, filed on Oct. 28, 1997, now abandoned.

(51) Int. Cl.[7] ................................................ G01N 21/61
(52) U.S. Cl. ........................................ 250/343; 250/338.5
(58) Field of Search .................................. 250/343, 338.5

(56) References Cited

U.S. PATENT DOCUMENTS

| | | |
|---|---|---|
| 5,060,508 | 10/1991 | Wong . |
| 5,163,332 | 11/1992 | Wong . |
| 5,222,389 | 6/1993 | Wong . |
| 5,340,986 | 8/1994 | Wong . |
| 5,341,214 | 8/1994 | Wong . |

*Primary Examiner*—Constantine Hannaher
(74) *Attorney, Agent, or Firm*—Pepper Hamilton, LLP

(57) ABSTRACT

A diffusion-type NDIR gas analyzer with an improved response time due to convection flow created by a temperature gradient between gas located within a waveguide and gas located within a diffusion pocket of space created between the waveguide and a semi-permeable membrane which surrounds the waveguide. The temperature gradient may be created by a thermally resistive radiation source that is not thermally isolated from the waveguide. The semi-permeable membrane is made of a hydrophobic material and has a thickness sufficient to provide its own structural integrity. The semi-permeable membrane can have a porosity less than approximately 50 microns and be comprised of ultra high molecular weight polyethylene or Teflon®.

20 Claims, 3 Drawing Sheets

DIFFUSION-TYPE NDIR GAS ANALYZER WITH IMPROVED RESPONSE TIME DUE TO CONVECTION FLOW

This application is a continuation of application Ser. No. 08/958,160, filed Oct. 28, 1997, now abandoned.

FIELD OF THE INVENTION

The present invention is in the field of diffusion-type Non-Dispersive Infrared ("NDIR") gas analyzers.

BACKGROUND OF THE INVENTION

NDIR gas analysis measures the concentration of a gas in a sample by determining the amount of absorption of light which occurs at wavelengths which are normally selected to coincide with a relatively strong absorption band that is characteristic of the gas to be measured. In its simplest form, an NDIR gas analyzer contains a radiation source, an optical interference filter, a sample chamber, a detector and associated electronics. In operation, light is emitted from the radiation source and passed through the sample chamber where a portion of the light is absorbed by a sample gas. Next, light is passed through the filter to remove undesired wavelengths of light and then the remaining filtered light is passed on to the detector which measures the strength of the filtered light. Finally, the associated electronics calculate the concentration of the gas being measured in the sample cell.

The theory of NDIR gas analysis is well established. It has long been considered one of the best methods for gas measurement. However, it is not suitable for many uses because of its complicated and expensive implementation. In designing a low cost NDIR gas analyzer, there are a number of trade offs in the design which must be evaluated and balanced for a particular end use. The optical scheme of the NDIR gas analyzer should be highly efficient and should provide the maximum possible signal on the detector. There should also be an efficient way to exchange gas inside the sample chamber with ambient gas through the diffusive material. However, the diffusive material should have enough density to protect the inside of the sample chamber from particles of dust. As a result, a good design should take the following limitations into account: (1) The density and the thickness of the diffusive material should be efficient to protect against dust and other unwanted particles. (2) The signal to noise ratio on the detector should be sufficient to measure the signals. (3) The power consumption of the source is limited, especially in the case of low power applications powered by a battery. (4) The response time of the sensor. And, of course, cost must be considered in meeting these limitations.

Over the years, various improvements have been made to simplify NDIR gas analyzers in order to reduce the cost of such devices. Examples of some improvements are set forth in U.S. Pat. Nos. 5,163,332, 5,222,389 and 5,340,986, all of which involve diffusion-type NDIR gas analyzers which rely upon a specularly reflective waveguide. Advantages of such devices are simplicity of design and cost. By relying upon diffusion to bring gas into the sample chamber, such devices eliminate the need for more complex and expensive components associated with NDIR gas analyzers which must rely on a pump to create a gas flow into and out of the gas sample chamber. By relying upon a waveguide, such devices use one of the most efficient ways to transport light from the source to the detector through the gas chamber. While such improvements have advanced the state of the art of NDIR gas analyzers, there are still many applications in which NDIR gas analyzers cannot be used when low cost is an integral design constraint, especially when a quick response time is required.

Accordingly, a continuing need exists for inexpensive NDIR gas analyzers. In addition, there is also a continuing need for further improvements in NDIR gas analyzers which will increase their response time in low cost applications.

SUMMARY OF THE INVENTION

The present invention is generally directed to an improved diffusion-type NDIR gas analyzer with an improved response time due to a convection flow created by a temperature gradient between gas located within the waveguide and gas located within a diffusion pocket of space created between the waveguide and a semi-permeable membrane which surrounds the waveguide.

In a first, separate aspect of the present invention, a semi-permeable membrane is provided which is made of a hydrophobic material with a thickness sufficient to provide its own structural integrity so that it can surround the waveguide and create a diffusion pocket of space between the membrane and the waveguide. The semi-permeable membrane can have a porosity less than approximately 50 $\mu$m, and a porosity of approximately 10 $\mu$m is especially advantageous. Suitable materials for making the semi-permeable membrane include ultra high molecular weight polyethylene or Teflon® (polytetraflourethylene), and the membrane may be injection molded. It has been found that back diffusion through the semi-permeable membrane effectively stops when gas is pumped into the waveguide.

In another, separate aspect of the present invention, a first aperture is located in a first portion of the waveguide and a second aperture is located in a second portion of the waveguide. The apertures are sized and spaced apart such that gas flow into the waveguide is assisted by a convection flow created by a temperature gradient. As a result of convection flow, it is possible to detect approximately 95% of the signal of a sample gas in less than approximately thirty seconds.

In still another, separate aspect of the present invention, a temperature gradient may be created by heat given off by a thermally resistive radiation source which is not thermally isolated from the sample chamber. This configuration also eliminates the need for a second window in the waveguide.

Accordingly, it is a primary object of the present invention to provide an improved diffusion-type NDIR gas analyzer with an improved response time.

This and further objects and advantages will be apparent to those skilled in the art in connection with the drawings and the detailed description of the preferred embodiments set forth below.

DETAILED DESCRIPTION OF THE PREFERRED EMBODIMENTS

Figure 1:
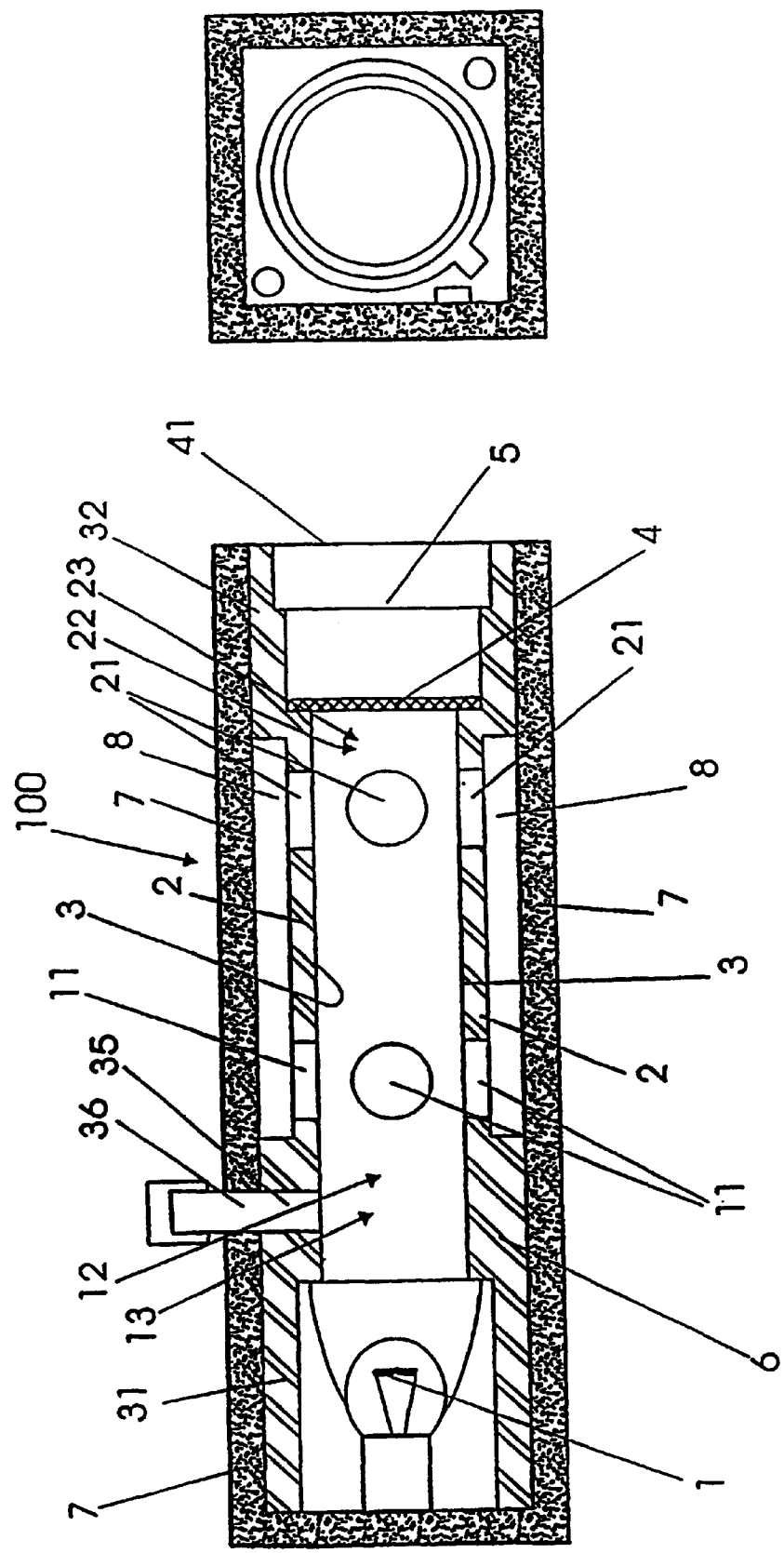
FIG. 1 is a drawing of a preferred embodiment of an analyzer made in accordance with the present invention.

In the preferred embodiment of the present invention shown in FIG. 1, a diffusion-type NDIR gas analyzer, generally designated as 100, has a linear optical path from the infrared source 1 through the waveguide, which is shown generally as 2, to the detector 5. The infrared source 1 is a thermally resistive radiation source, such as an incandescent light bulb. The waveguide has a specularly reflective surface 3 and includes a plurality of apertures which includes four apertures 11 located in a first end 12 of a first portion 13 of the waveguide 2 and four apertures 21 located in a second end 22 of a second portion 23 of the waveguide 2. The detector 5 is thermally isolated by a window 4 from the waveguide 2. Unlike most prior art waveguides, in an especially preferred embodiment for certain low cost applications, there is no window between the source 1 and the waveguide 2, which means that the source is not thermally isolated from the waveguide 2.

Figure 2:
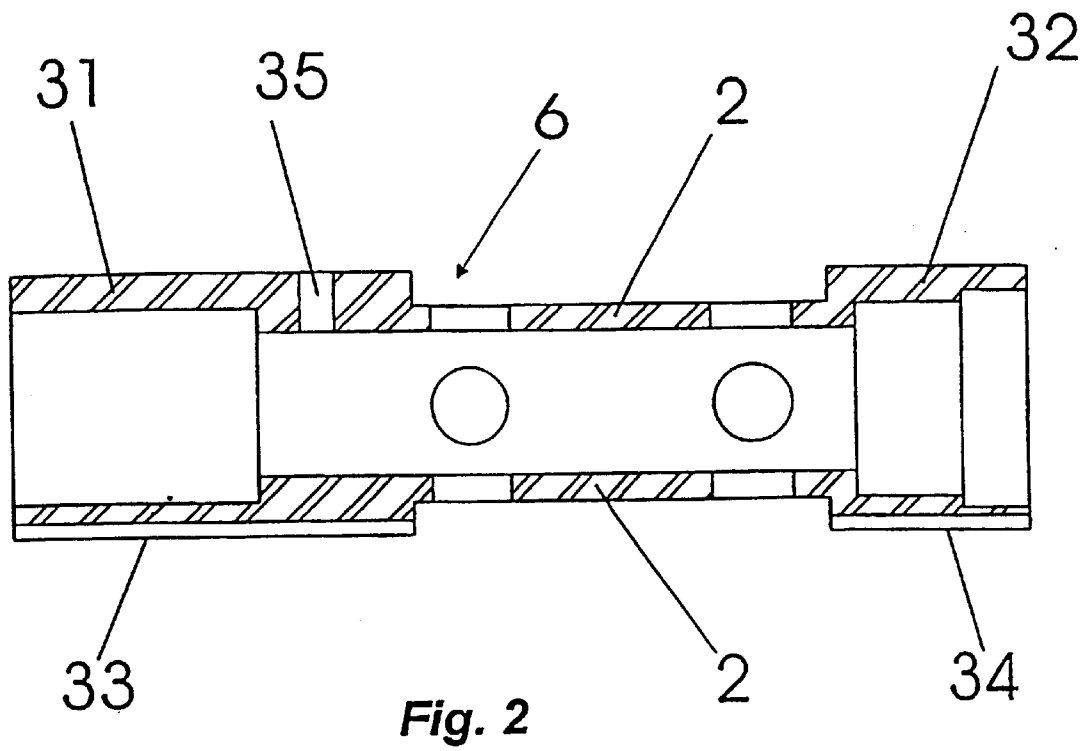
FIG. 2 is a drawing of an integral housing used in FIG. 1.

The waveguide 2 is part of a single integral housing 6 which includes a first end 31 and a second end 32 connected to the waveguide 2 as depicted in FIG. 2. While portions of the first or second ends 31 and 32 may function as part of the waveguide 2 since they can be specularly reflective, for ease of reference and clarity of understanding, the term "waveguide" shall hereinafter refer only to that portion of the housing which is located between the first or second ends 31 and 32. The lamp 1 is housed in the first end 31 while the window 4 and the detector 5 are housed in the second end 32. The housing 6 is inserted into a semi-permeable membrane 7 which surrounds the waveguide 2 and creates a diffusion pocket of space 8 between the membrane 7 and the waveguide 2. The membrane 7 is made of a hydrophobic material with a thickness sufficient to provide its own structural integrity which has been injection molded. Once the housing 6 is inserted into the membrane 7, only the outer or back end 41 of the second end 32 is not surrounded by the membrane. Accordingly, the first and second ends 31 and 32 are advantageously provided with channels 33 and 34 in which an electronic lead from the lamp 1 can be held as it travels from the outer end 41 of first end 31 to outside the outer end 42 of second end 32. The first end 31 also has a calibration aperture 35, which is aligned with a calibration aperture 36 in the membrane 7, which is blocked by a plug when not in use.

Flow of gas into the waveguide 2 is controlled by the area of the plurality of apertures in waveguide 2. The flow of gas is also controlled by the volume of the diffusion pocket 8 and the surface area of membrane 7.

The plurality of apertures located in the waveguide 2 are sized and spaced apart such that gas flow into the waveguide 2 is assisted by a convection flow created by a temperature gradient between gas located within the waveguide 2 and gas located within the pocket 8. In the past, the selection of the size and number of apertures used in a waveguide required a balancing of two competing factors. On the one hand, it is desirable that the total area occupied by the plurality of apertures be minimized so as to increase the efficiency of light transfer through the waveguide. On the other hand, the diffusion rate through the semi-permeable membrane is proportional to the area of the membrane, so it is desirable to have as large an area for diffusion as is possible. In order to balance these competing factors, the preferred embodiment of the present invention relies upon the creation of the diffusion pocket of space 8 between the membrane 7 and the waveguide 2. By creating this diffusion pocket of space 8, the effective area for diffusion will be almost as large as the outside area of the membrane which surrounds the waveguide. This helps to overcome the traditional trade off between maximizing the diffusion rate or maximizing light transfer The volume of the diffusion pocket of space 8 is determined by the distance of the membrane 7 from the waveguide 2. As shown in FIG. 1, the diffusion pocket 8 is defined by the membrane 7 and three portions of the housing 6, the first end 31, the second end 32 and the waveguide 2, because there is a snug fit between the first and second ends 31 and 32 and the membrane 7. Thus, it is possible to increase or decrease the volume of the diffusion pocket 8 and the surface area of membrane 7 by increasing or decreasing the size of the first and second ends 31 and 32 relative to the diameter of the waveguide 2. The volume of the diffusion pocket 8 is optimized when the exchange rate of gas from outside of the membrane 7 into the diffusion pocket and then into the waveguide is as fast as it could be with the chosen membrane and the size and form of the waveguide 2.

The membrane should have a porosity that will permit the gas to be measured to flow freely through the membrane, while at the same time keeping unwanted contaminants, such as dust, from passing through the membrane. It has been found that a membrane with a thickness of 0.05 inches ($1.27 \times 10^{-}$m), and a porosity of 50 $\mu$m or less, preferably of approximately 10 $\mu$m, provides very good empirical test results. More specifically, tests were performed using a membrane of ultra high molecular weight polyethylene with an average porosity of 10 $\mu$m and a thickness of 0.05 inches ($1.27 \times 10^{-3}$ m), manufactured by Interflo, Inc., material part number 38-244-2B, lot number 071797. The membrane was injection molded and had the configuration shown in FIG. 2, with the addition of four additional screw holes (not shown), two of which were located so as to be aligned with corresponding holes on opposite sides of first and second ends 31 and 32 of housing 6. (The purpose of the four screw holes is to fasten the assembly to a printed circuit board.)

Tests performed on semi-permeable membranes having a porosity of approximately 10 $\mu$m and approximately 50 $\mu$m revealed that back diffusion through the membrane effectively stopped when a test gas is pumped into the waveguide during calibration; back diffusion was not effectively stopped in tests performed on a semi-permeable membrane having a porosity of approximately 100 $\mu$m. When back diffusion is effectively stopped, calibration of diffusion-type NDIR analyzers is easier to achieve, at drastically reduced flow rates of up to $\frac{1}{100}$ what would be required when back diffusion is not effectively stopped.

Figure 3:
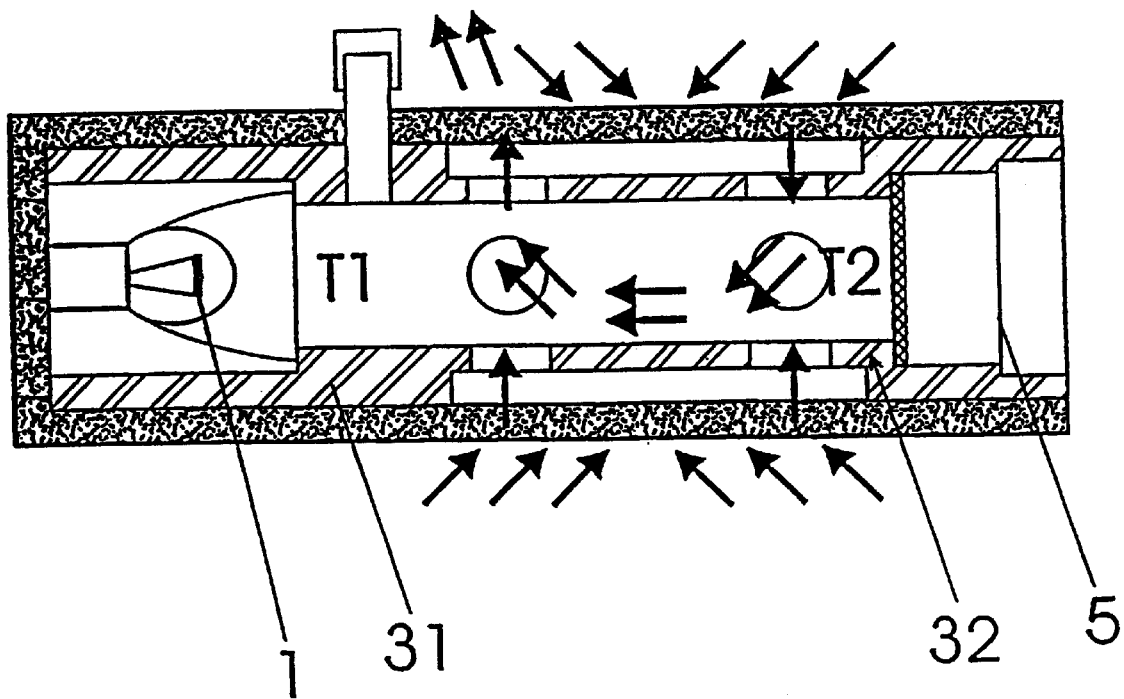
FIG. 3 is a schematic representation of convection flow when the analyzer shown in FIG. 1 is in operation.

Gas flow into the waveguide 2 is assisted by a convection flow created by a temperature gradient between gas located within the waveguide 2 and gas located within the diffusion pocket 8. The efficiency of the convection flow is maximized by locating apertures 11 and 21 close to opposite ends of the waveguide 2. The reason this location maximizes the efficiency is that there is a temperature gradient along the waveguide 2 because the first end 31 with source 1 has a temperature T1 that is hotter than the temperature T2 at second end 32 with detector 5 so that the pressure of gas at the first end 31 will always be less than the pressure of the gas at the second end 32. This will cause gas to flow from the second end 32 with detector 5 to the first end 31 with source 1, and the rate of flow will be proportional to the difference between the two temperatures. A schematic drawing illustrating gas flow associated with the analyzer 100 shown in FIG. 1 is set forth in FIG. 3.

A very fast response time for the analyzer 100 can be obtained by optimizing the various factors that affect flow of gas into the waveguide 2. The area of the plurality of apertures in the waveguide, the surface area of membrane 7, the volume of the diffusion pocket 8 and the volume of the waveguide 2 are balanced to provide the optimal rate of gas transfer from the ambient to the diffusion pocket 8 (using diffusion) then from the diffusion pocket 8 to inside of the waveguide 2 (using convection).

Figure 4:
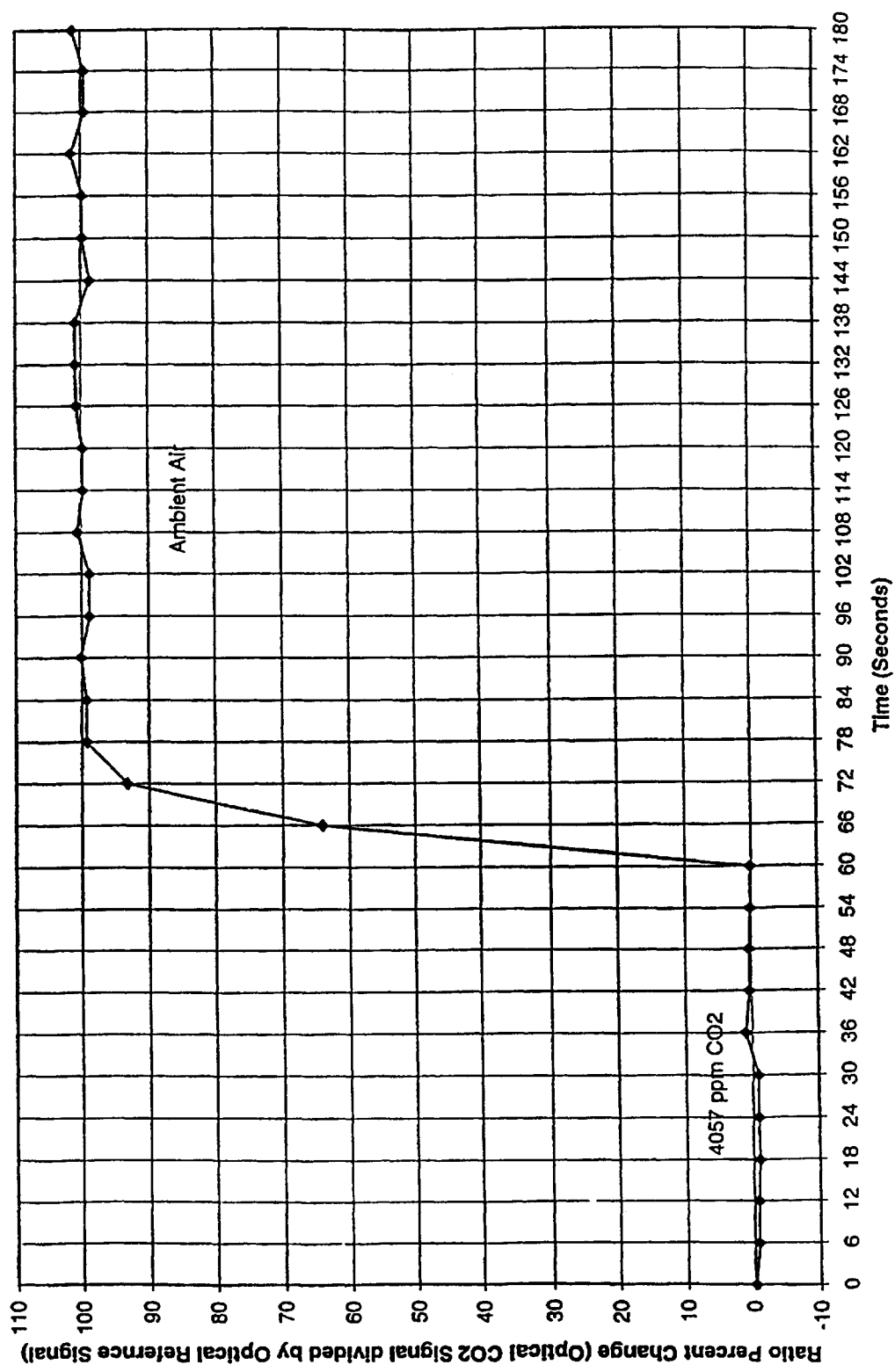
FIG. 4 shows normalized test data measuring response time of the preferred embodiment used to detect carbon dioxide.

FIG. 4 shows normalized data for a group of tests performed on sample gas analyzers for carbon dioxide made in accordance with the foregoing description of the preferred embodiment which used only one window and the 0.05 inch ($1.27 \times 10^{-3}$) thick membrane with a porosity of approximately 10 $\mu$m. To perform the tests, the sample gas analyzers were assembled and then the whole assembly was placed into a sealed clam shell type box. The size of the box was minimal. In practice, the box had dimensions of approximately 12 by 5 by 6 inches (30.48 cm×12.7 cm×15.24 cm). The box had all the electrical connections, so that the analyzers could run inside the box. The box also had a gas inlet and outlet. Initially, the box (with a working analyzer) was purged by carbon dioxide. In the specific tests shown in FIG. 4, a carbon dioxide concentration of approximately 4000 ppm was used, the flow rate being about 300 $cm^2$/min. The box was purged until the readings of the analyzer were stabilized, which typically took about 20 minutes. When the readings became stable, the gas flow was shut off and then the box was opened rapidly. Because the volume of the box was fairly small, the analyzer was rapidly exposed to ambient air. Then the readings of the analyzer were watched to see how fast the readings of the analyzer would reach the ambient level. The response time was measured as the time required to reach the 95% level of the difference between 4000 ppm and ambient. Using this procedure for measuring response time, the analyzer was able to detect approximately 95% of the signal of a sample gas in less than approximately fifteen seconds. Using this same procedure for measuring response time, it is desirable that a gas analyzer according to the present invention be designed to detect approximately 95% of the signal of a sample gas in less than approximately thirty seconds.

The above description of this invention is directed primarily to the preferred embodiment, and specifically to a preferred embodiment used to detect carbon dioxide. Further modifications are also possible in alternative embodiments without departing from the inventive concept. Thus, for example, an NDIR gas analyzer could include two windows, the second window thermally isolating the source from the waveguide, so long as a sufficient temperature gradient is still created between gas within the waveguide and gas within the diffusion space. Another example of a further modification is to use a non-linear optical path, such as an optical path described in either of U.S. Pat. Nos. 5,060,508 and 5,341,214.

Accordingly, it will be readily apparent to those skilled in the art that still further changes and modifications in the actual concepts described herein can readily be made without departing from the spirit and scope of the invention as defined by the following claims.

What is claimed is:

1. An improved diffusion-type Non-Dispersive Infrared gas analyzer, comprising:
   a specularly reflective waveguide with a plurality of apertures which includes a first aperture located in a first portion of the waveguide and a second aperture located in a second portion of the waveguide;
   an infrared source located proximate to a first end of the waveguide in the first portion of the waveguide;
   a window located in a second end of the waveguide in the second portion of the waveguide;
   a detector located proximate to the second end of the waveguide which is thermally isolated by the window from the waveguide;
   a semi-permeable membrane made of a hydrophobic material with a thickness sufficient to provide its own structural integrity which surrounds the waveguide and creates a diffusion pocket of space between the membrane and the waveguide;
   wherein the plurality of apertures are sized and spaced apart such that gas flow into the waveguide is assisted by a convection flow created by a temperature gradient between gas located within the waveguide and gas located within the pocket.

2. An improved diffusion-type Non-Dispersive Infrared gas analyzer as recited in claim 1, wherein the source is a thermally resistive radiation source.

3. An improved diffusion-type Non-Dispersive Infrared gas analyzer as recited in claim 2, wherein the thermally resistive radiation source is not thermally isolated from the waveguide.

4. An improved diffusion-type Non-Dispersive Infrared gas analyzer as recited in claim 3, wherein the convection flow is created by heat given off by the thermally resistive radiation source.

5. An improved diffusion-type Non-Dispersive Infrared gas analyzer as recited in claim 1, wherein the semi-permeable membrane has a porosity less than approximately 50 microns.

6. An improved diffusion-type Non-Dispersive Infrared gas analyzer as recited in claim 1, wherein the semi-permeable membrane has a porosity of approximately 10 microns.

7. An improved diffusion-type Non-Dispersive Infrared gas analyzer as recited in claim 1, wherein the semi-permeable membrane is comprised of ultra high molecular weight polyethylene or polytetraflourethylene.

8. An improved diffusion-type Non-Dispersive Infrared gas analyzer as recited in claim 1, wherein the semi-permeable membrane is injection molded.

9. An improved diffusion-type Non-Dispersive Infrared gas analyzer as recited in claim 1, wherein the diffusion rate into the waveguide allows the detector to detect approximately 95% of the signal of a sample gas in less than approximately thirty seconds.

10. An improved diffusion-type Non-Dispersive Infrared gas analyzer as recited in claim 1, wherein back diffusion through the semi-permeable membrane effectively stops when gas is pumped into the waveguide.

11. An improved diffusion-type Non-Dispersive Infrared gas analyzer as recited in claim 1, wherein the first aperture is located proximate to the first end of the waveguide and the second aperture is located proximate to the second end of the waveguide.

12. An improved diffusion-type Non-Dispersive Infrared gas analyzer, comprising:
   a specularly reflective waveguide with a plurality of apertures which includes a first aperture located in a first portion of the waveguide and a second aperture located in a second portion of the waveguide;
   an infrared source;
   a detector;
   a semi-permeable membrane made of a hydrophobic material with a thickness sufficient to provide its own structural integrity which surrounds the waveguide and creates a diffusion pocket of space between the membrane and the waveguide having two ends;
   wherein the infrared source and the detector are located relative to the waveguide so as to form an optical path from the infrared source through the waveguide to the detector; and wherein the plurality of apertures are sized and spaced apart such that gas flow into the waveguide is assisted by a convection flow created by a temperature gradient between gas located within the waveguide and gas located within the pocket.

13. An improved diffusion-type Non-Dispersive Infrared gas analyzer as recited in claim 12, wherein the semi-permeable membrane has a porosity less than approximately 50 microns.

14. An improved diffusion-type Non-Dispersive Infrared gas analyzer as recited in claim 12, wherein the semi-permeable membrane has a porosity of approximately 10 microns.

15. An improved diffusion-type Non-Dispersive Infrared gas analyzer as recited in claim 12, wherein the semi-permeable membrane is comprised of ultra high molecular weight polyethylene or polytetraflourthylene.

16. An improved diffusion-type Non-Dispersive Infrared gas analyzer as recited in claim 12, wherein the semi-permeable membrane is injection molded.

17. An improved diffusion-type Non-Dispersive Infrared gas analyzer as recited in claim 12, wherein the diffusion rate into the waveguide allows the detector to detect approximately 95% of the signal of a sample gas in less than approximately thirty seconds.

18. An improved diffusion-type Non-Dispersive Infrared gas analyzer as recited in claim 12, wherein back diffusion through the semi-permeable membrane effectively stops when gas is pumped into the waveguide.

19. An improved diffusion-type Non-Dispersive Infrared gas analyzer as recited in claim 12, wherein the first aperture is located proximate to the first end of the waveguide and the second aperture is located proximate to the second end of the waveguide.

20. An improved diffusion-type Non-Dispersive Infrared gas analyzer, comprising:

a specularly reflective waveguide with a plurality of apertures which includes a first aperture located in a first portion of the waveguide near a first end of the waveguide and a second aperture located in a second portion of the waveguide near a second end of the waveguide;

a thermally resistive infrared source located proximate to a first end of the waveguide in the first portion of the waveguide which is not thermally isolated from the waveguide;

a window located in a second end of the waveguide in the second portion of the waveguide;

a detector located proximate to the second end of the waveguide which is thermally isolated by the window from the waveguide;

a semi-permeable membrane made of a hydrophobic material with a thickness sufficient to provide its own structural integrity and a porosity less than approximately 50 microns which surrounds the waveguide and creates a diffusion pocket of space between the membrane and the waveguide;

wherein the plurality of apertures are sized and spaced apart such that gas flow into the waveguide is assisted by a convection flow created by a temperature gradient between gas located within the waveguide and gas located within the pocket and the diffusion rate into the waveguide allows the detector to detect approximately 95% of the signal of a sample gas in less than approximately thirty seconds but back diffusion through the semi-permeable membrane effectively stops when gas is pumped into the waveguide.

* * * * *